United States Patent
Stevick et al.

(10) Patent No.: US 7,620,209 B2
(45) Date of Patent: Nov. 17, 2009

(54) METHOD AND APPARATUS FOR DYNAMIC SPACE-TIME IMAGING SYSTEM

(76) Inventors: Glen R. Stevick, 1636 Walnut St., Berkeley, CA (US) 94709; David M. Rondinone, 614 San Fernando Ave., Berkeley, CA (US) 94708; Jerome R. Singer, 2917 Avalon Ave., Berkeley, CA (US) 94705; Matthew D. Rocklin, 31812 Pasco Alto Plano, San Juan Capistrano, CA (US) 92675

( * ) Notice: Subject to any disclaimer, the term of this patent is extended or adjusted under 35 U.S.C. 154(b) by 1199 days.

(21) Appl. No.: 10/966,095

(22) Filed: Oct. 14, 2004

(65) Prior Publication Data
US 2006/0082590 A1    Apr. 20, 2006

(51) Int. Cl.
*G06K 9/00* (2006.01)
(52) U.S. Cl. ......................... 382/106; 382/154
(58) Field of Classification Search ......... 382/106–108, 382/142–154
See application file for complete search history.

(56) References Cited

U.S. PATENT DOCUMENTS

| | | | | |
|---|---|---|---|---|
| 2,449,542 A * | 9/1948 | Ayres et al. | ................. | 342/180 |
| 3,694,205 A * | 9/1972 | Richardson, Jr. | ............ | 396/661 |
| 4,175,862 A * | 11/1979 | DiMatteo et al. | ........... | 356/610 |
| 4,645,348 A * | 2/1987 | Dewar et al. | ................ | 356/603 |
| 4,653,104 A * | 3/1987 | Tamura | ...................... | 382/154 |
| 4,752,964 A * | 6/1988 | Okada et al. | ................ | 382/154 |
| 4,825,263 A * | 4/1989 | Desjardins et al. | .......... | 356/603 |
| 4,867,570 A | 9/1989 | Sorimachi | | |
| 4,965,442 A * | 10/1990 | Girod et al. | ............. | 250/201.7 |
| 4,965,840 A * | 10/1990 | Subbarao | .................... | 382/106 |
| 4,979,815 A * | 12/1990 | Tsikos | ...................... | 356/3.06 |
| 5,003,166 A * | 3/1991 | Girod | ...................... | 250/201.4 |
| 5,006,721 A | 4/1991 | Cameron | | |
| 5,056,922 A * | 10/1991 | Cielo et al. | ................. | 356/604 |
| 5,102,223 A * | 4/1992 | Uesugi et al. | ............... | 356/607 |
| 5,125,741 A * | 6/1992 | Okada et al. | ............. | 356/237.2 |
| 5,175,601 A * | 12/1992 | Fitts | ........................... | 356/604 |
| 5,195,030 A * | 3/1993 | White | ......................... | 705/26 |
| 5,243,665 A * | 9/1993 | Maney et al. | ............... | 382/152 |
| 5,249,045 A * | 9/1993 | Lemelson | .................... | 348/92 |
| 5,280,436 A * | 1/1994 | Kubota et al. | .............. | 700/302 |
| 5,283,641 A * | 2/1994 | Lemelson | .................... | 348/92 |

(Continued)

OTHER PUBLICATIONS

Vuylsteke/Oosterlinck,Range Image Acquisition with a Single Binary-Encoded Light Pattern,IEEE Transactions on Pattern Analysis&Machine Intell., Dec. 1990, p. 148-164, vol. 12,No. 2.

(Continued)

*Primary Examiner*—Manav Seth
(74) *Attorney, Agent, or Firm*—Howard Cohen (57) ABSTRACT

A method for creating a 3D map of the surface contours of an object includes projecting a variety of patterns onto the object, and imaging the patterns as they fall on the object to encode the topographic features of the object. The images are processed in a computer program in a manner such that a complete 3D map of the surface of the object is obtained in digital form. Reiteration of the method can detect motional variation such as a breathing human, flexure of a complex mechanical structure, or a stress-strain testing of an airplane, vehicle, beam, bridge, or other structure.

23 Claims, 11 Drawing Sheets

U.S. PATENT DOCUMENTS

| | | | | |
|---|---|---|---|---|
| 5,305,092 | A * | 4/1994 | Mimura et al. | 356/609 |
| RE34,749 | E * | 10/1994 | Leong et al. | 250/237 G |
| 5,361,308 | A | 11/1994 | Lee | |
| 5,589,942 | A * | 12/1996 | Gordon | 356/611 |
| 5,748,865 | A * | 5/1998 | Yamamoto et al. | 345/423 |
| 5,753,931 | A * | 5/1998 | Borchers et al. | 250/559.22 |
| 5,831,736 | A * | 11/1998 | Lichtman et al. | 356/613 |
| 5,852,672 | A * | 12/1998 | Lu | 382/154 |
| 5,862,252 | A * | 1/1999 | Yamamoto et al. | 382/154 |
| 6,043,891 | A | 3/2000 | Hartrumpf | |
| 6,167,151 | A * | 12/2000 | Albeck et al. | 382/154 |
| 6,205,243 | B1 * | 3/2001 | Migdal et al. | 382/154 |
| 6,346,949 | B1 * | 2/2002 | Fujiwara et al. | 345/589 |
| 6,407,817 | B1 * | 6/2002 | Norita et al. | 356/608 |
| 6,442,476 | B1 * | 8/2002 | Poropat | 701/207 |
| 6,495,848 | B1 * | 12/2002 | Rubbert | 250/559.22 |
| 6,501,554 | B1 | 12/2002 | Hackney | |
| 6,510,244 | B2 * | 1/2003 | Proesmans et al. | 382/203 |
| 6,618,123 | B2 * | 9/2003 | Uomori et al. | 356/3.12 |
| 6,648,640 | B2 * | 11/2003 | Rubbert et al. | 433/24 |
| 6,705,526 | B1 * | 3/2004 | Zhu et al. | 235/472.01 |
| 6,754,370 | B1 * | 6/2004 | Hall-Holt et al. | 382/106 |
| 7,064,810 | B2 * | 6/2006 | Anderson et al. | 356/5.01 |
| 7,103,212 | B2 * | 9/2006 | Hager et al. | 382/154 |
| 7,140,544 | B2 * | 11/2006 | Smith et al. | 235/462.01 |
| 7,206,717 | B2 * | 4/2007 | Hardy | 702/152 |
| 7,423,658 | B1 * | 9/2008 | Uomori et al. | 345/660 |
| 7,447,558 | B2 * | 11/2008 | Pratt | 700/118 |
| 7,474,803 | B2 * | 1/2009 | Petrov et al. | 382/285 |
| 2002/0049530 | A1 * | 4/2002 | Poropat | 701/207 |
| 2003/0067537 | A1 * | 4/2003 | Myers | 348/47 |
| 2003/0071194 | A1 * | 4/2003 | Mueller et al. | 250/208.1 |
| 2005/0002544 | A1 * | 1/2005 | Winter et al. | 382/104 |
| 2005/0059886 | A1 * | 3/2005 | Webber | 600/426 |
| 2005/0128197 | A1 * | 6/2005 | Thrun et al. | 345/421 |
| 2005/0180623 | A1 * | 8/2005 | Mueller et al. | 382/154 |

OTHER PUBLICATIONS

Weng/Cohen/,Camera Calibration with Distortion Models & Accuracy Evaluation, IEEE Transactions on Pattern Analysis&Machine Intelligence, Dec. 1992, p. 965-980, vol. 14,No. 10.

Vuori,Three dimensional imaging system with structured lighting and practical constraints, J Electronic Imaging, Jan. 1997, p. 140-144 vol. 6(1).

Sansoni,Three-dimensional vision based on a combination of graycode . . . systematic errors, Applied Optics, Nov. 2001, p. 6565-6573, vol. 38, No. 31.

Sansoni, Calibration and Performance Evaluation of a 3-D Imaging Sensor . . . Structured Light, IEEE Trans.on Instrumentation and Measurement, Jun. 2000, p. 628-636, vol. 49, No. 3.

Heikkila, Geometric Camera Calibration Using Circular Control Points, IEEE Trans.on Instrumentation and Measurement,Oct. 2000, p. 1066-1077, vol. 22, No. 10.

Sansoni, OPL-3D: A novel, portable optical digitizer for fast acquisition of free-form surfaces, ??, ??, p. 2593-2605.

* cited by examiner

METHOD AND APPARATUS FOR DYNAMIC SPACE-TIME IMAGING SYSTEM

CROSS-REFERENCE TO RELATED APPLICATIONS

Not applicable.

FEDERALLY SPONSORED RESEARCH

Not applicable.

SEQUENCE LISTING, ETC ON CD

Not applicable.

BACKGROUND OF THE INVENTION

1. Field of the Invention

The present invention relates to an apparatus and method for producing a rapid time-related three dimensional image with a numerical profile of an object. More particularly, it involves projecting complex digitally based patterns or scanning laser beam(s) on to the object, photographing these patterns with a fast response digital camera, and rapidly calculating a dimensional map of the contours, edges, and openings of the object.

2. Description of Related Art

In 1905, Albert Einstein, who at that time was a patent examiner in Zurich, developed the Special Theory of Relativity which emphasized the importance of considering time in addition to the three dimensions of space in describing the behavior of matter and energy. In accordance with this concept, creating three dimensional profiling images in a very short time period is very useful in order to record a plethora of fundamental dynamic observations in physics, chemistry, biology, microscopy, medicine, and engineering. It also has a particular application to identification procedures for security applications.

Stereoscopic photography was invented in the nineteenth century, and has been developed since then to create very colorful stereoscopic movies. In contrast, the development of stereoscopic profiling with accurate detailed measurements of three dimensional objects has been difficult to achieve. The development of digital photography and fast computation using fast digital processing has now provided the possibility of accurate stereoscopic imaging with detailed dimensional measurements of the contours of an object in real time.

Presently used techniques for non-invasive three dimensional imaging with digital detailing of an object utilize a variety of systems. One technique is the use of time of flight of a pulsed laser whereby the distance from the laser to the object is determined by measuring the transit time of the laser beam. This procedure, described by Cameron, et al in U.S. Pat. No. 5,006,721 provides fairly accurate digital topographical data. A commercial version of the laser ranging system is manufactured by Cyrax Technologies, and several other companies. While such systems provide good three dimensional data, they involve a quite costly apparatus because the time of flight must be measured to a few picoseconds, and the mirrors used to direct the laser beam as well as the mirrors used to route the reflected beam must be exact to a small division of a minute of arc. In addition, the scanning of a three dimensional object with a laser beam requires a considerable length of time, due to the fact that each incremental point on the surface of an object must be illuminated by the beam and the time of flight measured, resulting in a finite (and relatively long) time for all points to be illuminated and surveyed.

Another technique is the use of stereographic projections of a grid. This procedure, as described by M. Proesmans, et al. In U.S. Pat. No. 6,510,244 B2, issued Jan. 21, 2003, describes the use of a projected grid for topographic imaging. They describe a grid projection with a camera directed to provide three dimensional imaging. The use of such relatively static methods does not provide for the real-time measurement of dynamic details needed for dynamically imaging and measuring surface contour dimensions of objects which have movement, such as a bridge or beam undergoing stresses and strains. As stated in their patent, their application is "aimed at showing and not measuring the object."

Applications such as rapid reverse engineering with dynamic considerations of stress-strain relationships, measurements of flexure of mechanical and civil structures such as airplanes, vehicles, bridges, pipes, pipelines, steel tanks, autos and ships require very fast imaging techniques for which this invention is designed and applicable. In such applications as human body imaging where, due to breathing and heart motion, it is important to consider the time aspect of imaging in order to acquire realistic measurements of the body. There is a need for such rapid imaging procedures in medical analyses, for example, in following the progress, and in determination of the efficacy of treatments of such diseases as osteoporosis and skin cancers as well as other skin and body medical problems.

BRIEF SUMMARY OF THE INVENTION

The present invention utilizes a method for dimensional measurement of the surface contours of an object. The method employs selective computer controlled projection of a variety of patterns onto the object, and imaging of the patterns as they fall on the object to encode the topographic features of the object. The object can have a motional variation such as a breathing human, a complex flexing civil or mechanical structure, or a stress-strain testing of an airplane, vehicle, beam, bridge, or other structure. The images of the object are collected by a digital camera, and are processed in a computer program in a manner such that a complete three dimensional map of the surface of the object is obtained in digital form. In order to facilitate precision, the system may generate a digital pattern which is projected onto the object in a manner so that the pattern configuration provides the data for a computer program to determine exact dimensions. The system may also use a laser source of radiation by scanning the object rapidly using a laser beam. By utilizing a rapid procedure, the data provides a measure of the time variations of the size of the object. The usual output of the digital system supplies a three dimensional true color image as well as exact dimensional data on the depth, width, height and contours of the surface of the object.

The invention is particularly applicable to imaging of humans for medical analyses. Some examples: for full body inspection for skin cancer wherein the size of skin malignancies can be monitored, for breathing patterns, for reconstructive surgery, for dental analyses of the jaw, individual teeth, and bite, for facial reconstruction, and for gait analysis. It is applicable to design and manufacture of prosthetic units. Likewise, the invention may be used to monitor the changes in the body over time to assess the efficacy of weight loss programs, body building efforts, and the like. The system is also applicable for body measurements for the fitting of custom clothing and custom shoes, wherein all dimensions of the body are acquired, and clothing patterns may be modified in every dimension for optimal fit.

The present invention is designed to determine exact measurements as distinguished from relative topographies. In order to carry out such exact measurements, a range finder system and/or a standard fiducial object is utilized in the system so that absolute dimensions are determined.

The invention is also useful for identification and recognition for security applications, as it can provide motion detection and triggered three dimensional mapping of an intruded area. Also it is very applicable to accident analyses and prediction of mechanical failure where dimensional changes in mechanical structures may be analyzed in three dimensions. The invention is also very useful in imaging the holds of ships, planes, freight trains, and warehouses, where the images may yield numerical values for the exact amount and distribution of space available for use, or when partially loaded, for a determination of the space available fur further use. Another application is to security in examining the cargo space in ships, trucks, planes, and other compartments: by determining the volume numerically exactly, the existence of hidden compartments can be found. Another application is to microscopy. Here the three dimensional sizes of the object, (for example, a microbe), are readily determined, and the mobility of the microbe may be measured. Recent research also indicates that weaponized microbes in a cloud can be identified by the reflected light spectrum and by the change in shape of a cloud. This invention provides a significant advantage over the usual two dimensional measurements used for microscopic analyses.

By utilizing a plurality of distinct wavelengths within the electromagnetic spectrum, with the appropriate projectors and digital cameras, infrared, ultraviolet, or any special type radiation may be utilized to acquire and reconstruct three dimensional images. The use of infrared is particularly appropriate for obtaining three dimensional thermal images which provide important information about temperature variations in humans, animals, electronic equipment, and mechanical structures. For such applications, the projector(s), and digital camera(s) are equipped with sensors sensitive to infrared. Another application is in inspection of manufactured products. Misalignments, displacements, or other defects are readily detected by comparison of the three dimensionally mapped color image with a stored image of the correctly configured product. One such immediate use is applicable to manufactured items such as integrated circuit inspection. Another immediate use is in the production of wallboard (or sheetrock), in which each sheet must be examined for superficial imperfections as well as surface non-planarity. Currently wallboard sheets are examined inch by inch by a scanner system, but a single imaging sequence of this invention at high speed may check an entire sheet at once.

DETAILED DESCRIPTION OF THE INVENTION

Figure 1:
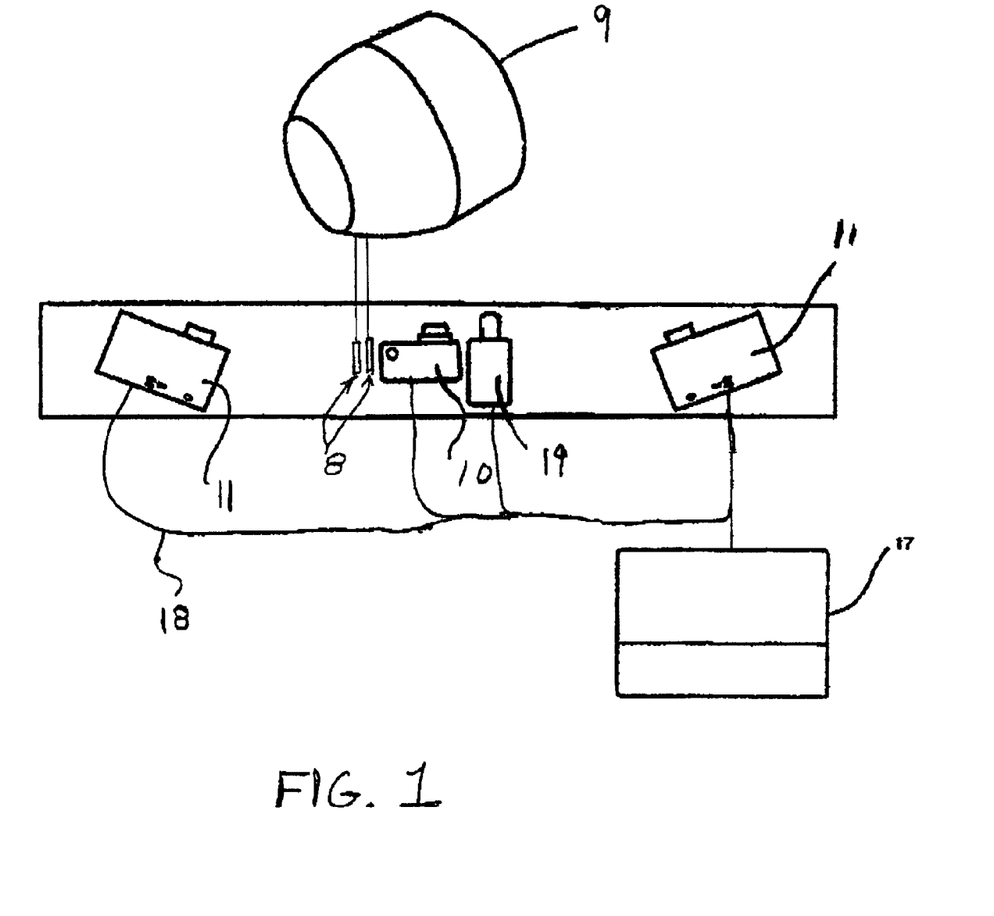
FIG. 1 is a schematic overhead view of a layout of a single camera, two projector imaging system designed for rapid three dimensional dynamic imaging in accordance with the present invention.

The present invention generally comprises a method for generating a dimensional map of the surface of an object, and analyzing the dimensional data to examine the object in useful ways. Referring to FIG. 1, the method involves providing a pair of projectors 11, each of the projectors directed to project a pattern of lines on an object 9. The type of projector utilized may be a conventional type or a digital type. The projectors are spaced apart to illuminate differing aspects of the object. A digital camera 10 is directed at the object 9 to acquire images of the object, and the configuration of the projected patterns on the surface of the object. The images are fed to computer 17 which processes the images to generate a dimensional map that numerically describes the contours, edges, openings, and surface features of the object 9. A range finder 19 is also directed toward the object to obtain at least one absolute measurement of the distance of the apparatus to the object, upon which the relative values of the dimensional map may be accurately based.

By using multiple projectors 11 and the camera 10, the images generated by the camera can readily be processed in a manner wherein they mesh together seamlessly, and a full three dimensional digital image of the object 9 is obtained. The apparatus may be rotated about the object, or vice versa, so that all the surface of the object 9 may be imaged and dimensionally mapped, if desired or necessary. The projectors, camera, and the range finder 19 are all under the control of the computer 17 which sends out control signals and also receives the imaging data which it processes to obtain a complete three dimensional image. The seamless joining of the different views is accomplished in software by observing that when several adjoining profiles from the different views are identical, then that is the seam between those views, and the different views are then joined in the display and in the numerical values of the stored profile information.

The range finder 19 is an option which can be a laser or other type of device, and can be incorporated into the camera and/or the projectors. It may be utilized to provide an independent fiducial range and size determination which can be used to obtain exact dimensions of the object. Its modes of operation and the range are controlled by the computer 17. The range data is sent back to the computer controller through the cable 18. The computer may then use that information to provide focusing information for the projector lenses. Another method of determining the exact fiducial measurements of an object is by initially scanning an object with well known dimensions. The system uses that scan as a calibration for further scans. Another means of providing a measurement of size utilizes a laser with a beam splitter or two lasers 8 which project two spots or crosses from two parallel beams. The distance between the beams is established by the geometry of the beam splitter and mirrors. The distance between the spots or crosses projected by the laser 8 on the object is then determined as an absolute measure.

The computer program used to process the images of the patterns projected on the object 9 obtained by the digital camera 10 utilizes the shapes of the projected lines to determine the curvatures, edges, openings, and hills and valleys of the object. The computer 17 is programmed to carry out the mathematical function that determines the numerical profiles of the object. In order to obtain a sharp focus of the projector images, the camera, which is easily automatically focused, may also provide a focusing signal for the projector focusing system thereby providing sharp patterns to facilitate the three dimensional map determination.

The projectors 11 and the camera 10 are specified to operate using any of several types of radiation. White light is used when true color image construction is desired. However, in some instances, infrared, ultraviolet, laser, or X-ray radiation are of more importance or of more interest in imaging. The cameras and projectors may be utilized for such procedures by simply substituting infrared, ultraviolet, or X-ray sensitive cameras, projectors, and range finders as appropriate to the wavelength utilized.

The projectors 11 are programmed by the computer 17 through the cable 18 to provide a series of patterns having lines extending vertically and/or horizontally which are bent or deformed when they are projected onto the surface of the object. The digital camera 10 receives the image of these deformations in the numerically ordered pixels of its photosensor, the pixel data being in the form of numbers which determine the entire topography of the object. These ordered numbers are then transmitted via the cable 18 to the computer 17 which processes and assembles these numbers to provide the complete dimensionally mapped topographic image of the object. The computation may be accelerated, if necessary, by using multiple processors coupled together. The cost of such high speed computation has become quite reasonable due to progress in computer manufacturing.

In order to obtain dynamic or motional information, once the sequence of patterns have been generated and recorded, a single pattern is projected continuously on the object 9. The pattern image caused by the topography of the object being scanned, which may vary in time, is then digitally acquired at a fast frame rate which, depending upon the type of digital camera, may be 30 times per second, hundreds of times per second, or more).

The variations of the dimensions of the object, as revealed by successive dimensional maps taken over time, provide a time sequence of the dynamic changes of the object.

In reconstructing the image from the calculated dimensional map, a spline fit is utilized to smooth the digital data. This results in a type of "best average" for the image display, and the image is presented smoothly rather than as discrete steps common to some digital displays.

In addition, to increase the speed of image acquisition, we utilize the projection of multiple patterns superimposed upon each other projected simultaneously, thereby reducing the number of digital images required to accumulate all of the data to generate the complete image. The superposition of all of the projected patterns utilizes a number of different wavelengths (colors in the visible range) in the projector. Different line patterns may be projected in different colors, and the digital camera is then utilized to separate the different colors, and thereby speed up the imaging process.

Figure 2:
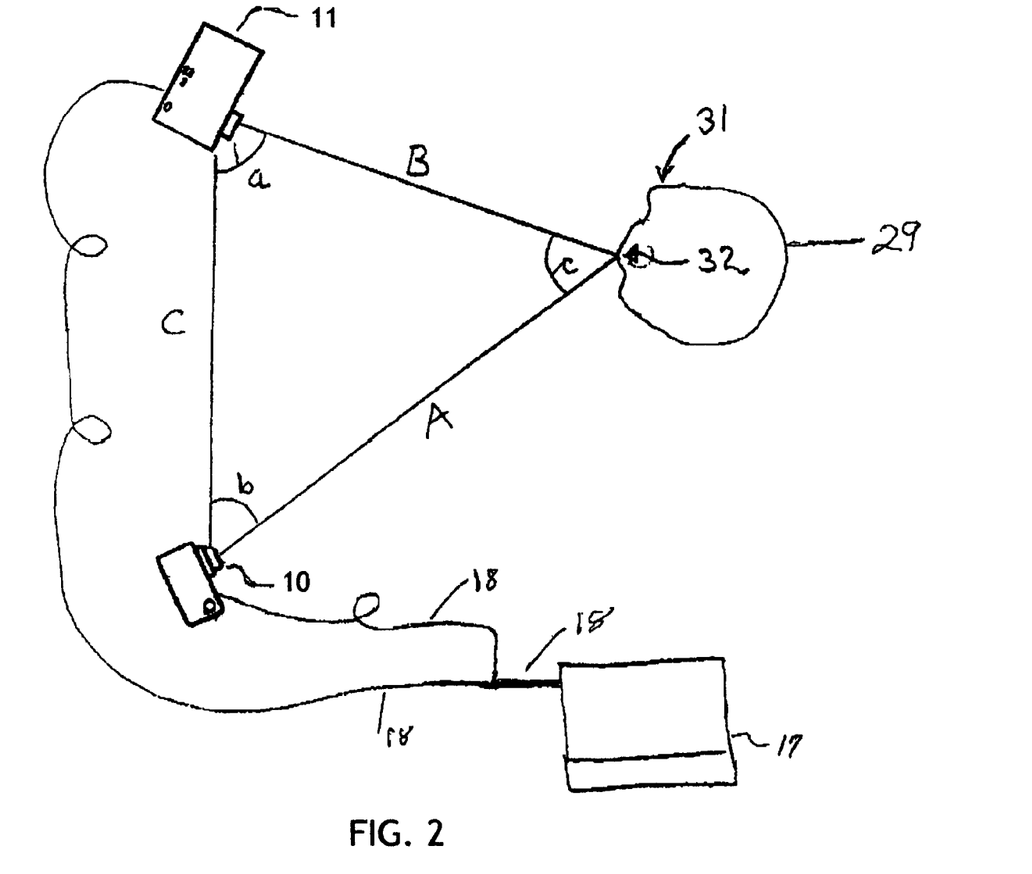
FIG. 2 is a schematic view of the geometry of the imaging system of the invention showing the triangulation procedure utilized to obtain an image of the exact profiles of a three dimensional object.

Referring to FIG. 2, the fundamental measurement of the exact distance from the camera receptor plane to the object utilizes a trigonometric solution of the oblique triangle, one side of which B is formed by the light ray B projected by the projector 11 to the point 32 on the surface 31 of the object 9. The digital camera 10 receives reflected light from that point 32 along the direction A which forms a second side of the triangle. The distance C which forms the third side of the triangle is the exact distance between the projector and the camera. The angles a and b of the triangle are known quantities because they are established by the geometry of the setup and the digital information supplied to the projector and received by the camera. Therefore, using trigonometry, the digital computer 17 calculates the exact distance A from the camera receptor 10 to the object surface 32 using the following formula:

$$A = C \sin a / (\sin c) \tag{1}$$

Since C, the distance between projector and the digital camera is known, and angles a and c, the angles of the directions of the projector and the digital camera are known, the calculation is rapid and straightforward. The computer calculation is facilitated by having the sine values in memory so that the sines of the angles are rapidly accessed. In this invention, the values of all the distances to the object are simultaneously calculated for all of the pixels of the camera, each of which are, in general, different values. This separation of all of the distances to the different picture elements (pixels) of the digital camera occurs through the fact that each pixel (the smallest useful image increment) provides its individual value for the distance to the object because of the geometry of the photosensitive receptors of the digital camera. In other words, the individual pixels are processed by the formula (1), and provide a complete set of distance values simultaneously.

In order to carry out all the calculations for all of the points on the surface rapidly, it is necessary to carry out many calculations almost simultaneously. This is accomplished by projecting many lines on to the surface of the object, and using the digital camera which, due to its numerical pixel construction, automatically labels each individual point. All of these points are then transmitted to the very fast computer 17 which assembles the point calculations of distance, (from the camera to the surface of the object), into the complete image. This procedure provides a complete profiling of the three dimensions of the surface of the object (a three-dimensional map), including all the hills and valleys, edges and openings of the surface of the object 9 (or 29).

In general, object surfaces are time dependent, as for example, a stress-strain relationship or some other time dependent induced variation or motion. To measure these time dependent effects, first the complete image is calculated, and in the final step of that procedure, the projector projects many fine lines at one time on the object surface. All of the distances to every point on those lines are accumulated in the computer memory. When the object surface flexes or moves in any mode, the line pattern changes its curves and distorts proportional to the nature of the surface change. The digital camera records all of the variations and transmits it to the computer 17. The computer compares the new data with the stored data. This comparison is a very fast procedure for a computer. Using this procedure, the measurement of time dependent changes of the object surface 31 are very fast; the limitation on the speed of imaging time-dependent changes in the object is the speed of available digital cameras which, at the present time, can be considerably faster than one hundredth of a second, and even one thousandth of a second.

Several procedures are used to scale the three dimensional object. An object of known size, for example a ball may be temporarily used as the object. The ball is then scanned and the dimensions stored. This scaling procedure provides a fiducial scale for the computer which is then used to specify all of the dimensions of the next object 9. Another scaling procedure is to project a known spot size on the object. In addition, scaling may be accomplished by placing a measured surface or ruler on the object 9 surface.

A series of ten patterns of lines may be projected to achieve high accuracy. These sets of lines can be in ten separate black and white images or compiled and superimposed on each other, one set of lines for each color channel of red, green and blue. This allows for nine patterns of lines to be compacted to only three images. A neutral gray picture is also taken without lines being projected so as to establish and remove initial lighting conditions and discolorations of the scene. Additionally this allows for a third pattern type which uses a white, black, and also a third gray intensity level. This, along with using three patterns in each of the three color channels creates the ability to project twenty-seven individual lines in a singular picture. If time is an issue and the density of lines within each picture must be increased, then there is a fourth channel of light which can be utilized, polarization. By using a triply polarized plate in front of the LCD and two separate cameras with different polarizations the amount of lines resolved can be tripled for a single image, bringing the total number of patterns resolved to eighty-one. This single shot image is sufficiently accurate for many of the aforementioned applications where time and continuity of movement is an issue.

In order to have a reference image, a mathematical procedure is utilized which places an imaginary plane in the scene, solves for its expected values, and uses it as the reference. This solution both greatly decreases noise and halves the number of images, and thus time required. Mathematical logic is included to remove the effect of perspective inherent in cameras. The camera "sees" close objects as larger and farther objects as smaller. Since the 3D imaging system has recorded the distances to objects it can correct for this inaccuracy. Because modern photoreceptors have greater resolution than current LCD projectors and other types of projectors, the system uses the camera's increased level of detail to augment the level of accuracy provided by the LCD or other types of projectors alone. Logic is included which regards each resolved line from the projector as a discrete block of many pixels and, after analysis, smoothes these pixels intelligently using conventional spline fitting procedures.

Figure 3:
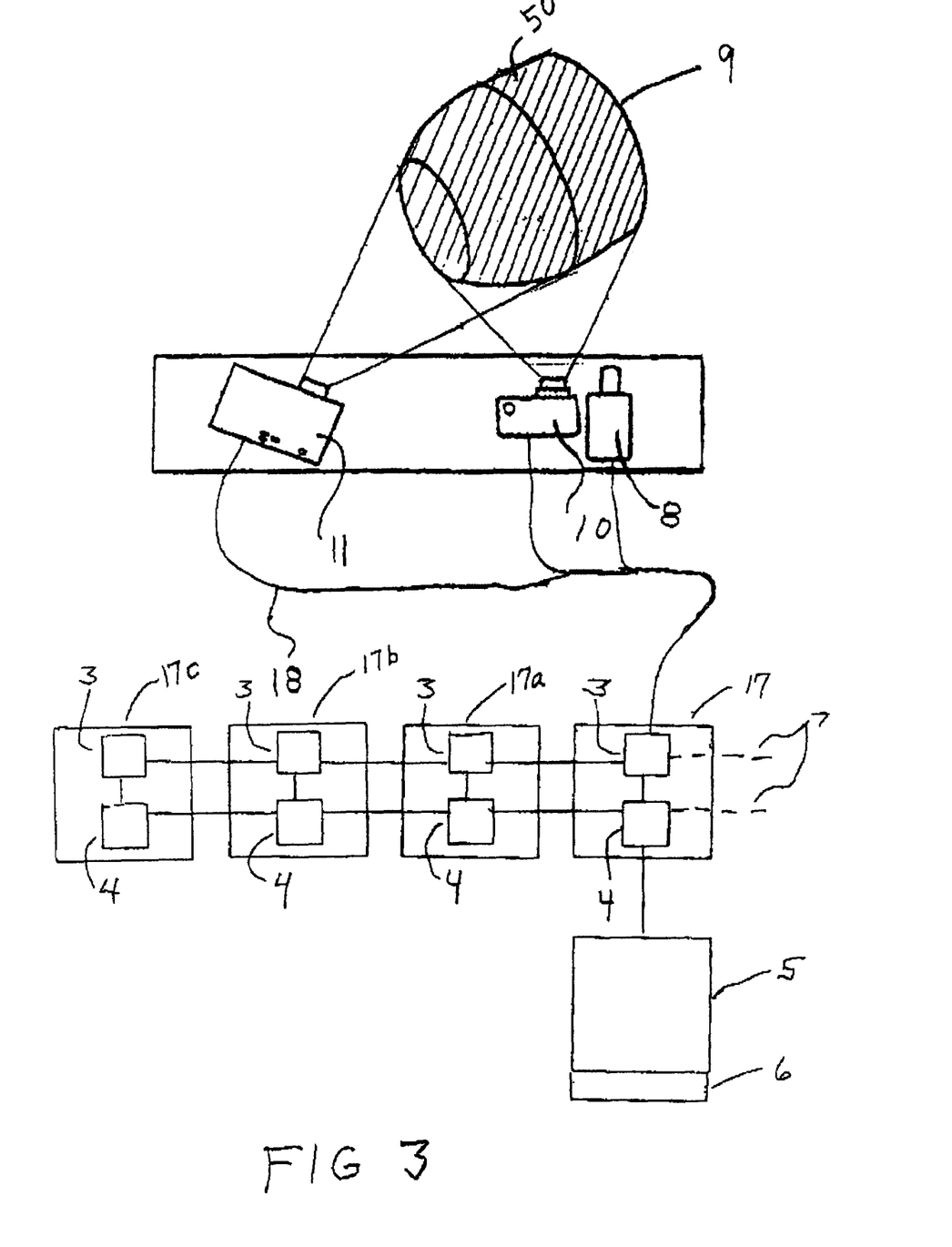
FIG. 3 is a schematic view depicting a multi-processor layout for high speed image acquisition and conversion to three dimensional data.

Referring to FIG. 3, the lines 50 projected onto the object 9 by the projector 11 are very closely spaced and provide the basis for a very fast imaging procedure. These are projected as a set of very fine lines, and are perceived by the digital camera system as a large collection of points because of the fundamental nature of the image receptor which is divided into picture elements, (pixels). With a digital camera system having 10 million pixels, for example, the camera receives 10 million points of excitation each of which has an exact geometric relationship through Formula (1) to the angle of the lines from the projector. Each of these 10 million pixels transmits its value directly to the computer memory 17 which interprets each value according to formula (1) as the actual distance from the camera photoreceptor to the to the surface of the object 9. The computer calculation is almost instantaneous due to the fact that the computer memory holds all of the sine values for immediate access. The procedure is extremely fast; and may be considered as happening in real time. The transformation of the calculated distances into the actual numerical profile values of the three dimensional map is also very fast because that only requires a scaling factor. The scaling factor is a simple multiplication factor for the computer and that calculation takes place in less than a millisecond.

The scaling factor is obtained by an initial observation of a specific projected line which is detected by the digital camera and then calculated through formula (1). Alternatively, the scaling factor can be obtained by imaging an object which has an exactly known size, or by using a projected scale.

Once the entire calculation of the profile (a dimensional map of the surface) of the object is obtained, the time variations of the size of the object can be very readily calculated because the time changes in the pixels of the camera change the values transmitted to the computer memory, and these changes are immediately recorded by the process of subtracting the values of each set of data points from the values of the prior set of data points. In the computer, the subtraction operations are extremely rapid by the nature of computer design.

The computer utilized can be a very fast computer, but it is more economical to couple a number of computers 17, 17a, 17b, 17c, (and as many as one desires for the selected computer speed) together as shown schematically in FIG. 3. Each of the computers is coupled together via high speed network cabling, and a high speed network switch within the memory compartment 3, and the central processing modules 4. The coupling allows all of these computers to work in unison and provide very fast calculations. The terminal display 5 and the keyboard 6 provide a control and response display. The dotted line 7 indicates that the system is not limited to four computers, but may be extended to more computers if additional speed is desired.

The features regarding the speed of this system provides a basis for dynamic imaging, which allows for the following applications in addition to being able to very rapidly provide imaging of non-dynamic objects.

1. Dynamic observations and measurements of deformation of aircraft wings under stress-strain conditions.
2. Dynamic observations and measurements of deformations of bridges and other structures under stress-strain loading conditions.
3. Dynamic observations, measurements, and detection of moving objects for security purposes.

4. Dynamic observations and measurements of human bodies including the aspects of breathing and movement.
5. Dynamic observations and measurements of objects which fail under load, with determination of the failure mode.
6. Dynamic observations and measurements of humans for security analyses and identification based on three dimensional images.
7. Dynamic motion studies with numerical analyses with application to human walking, human prosthetic design, human medical condition analyses.
8. High speed quality control processing in which a product such as wallboard or sheetrock is examined by the system of the invention, the entirety of each sheet being examined at once in a single imaging sequence and analyzed for surface defects or surface non-planarity.

Figure 4:
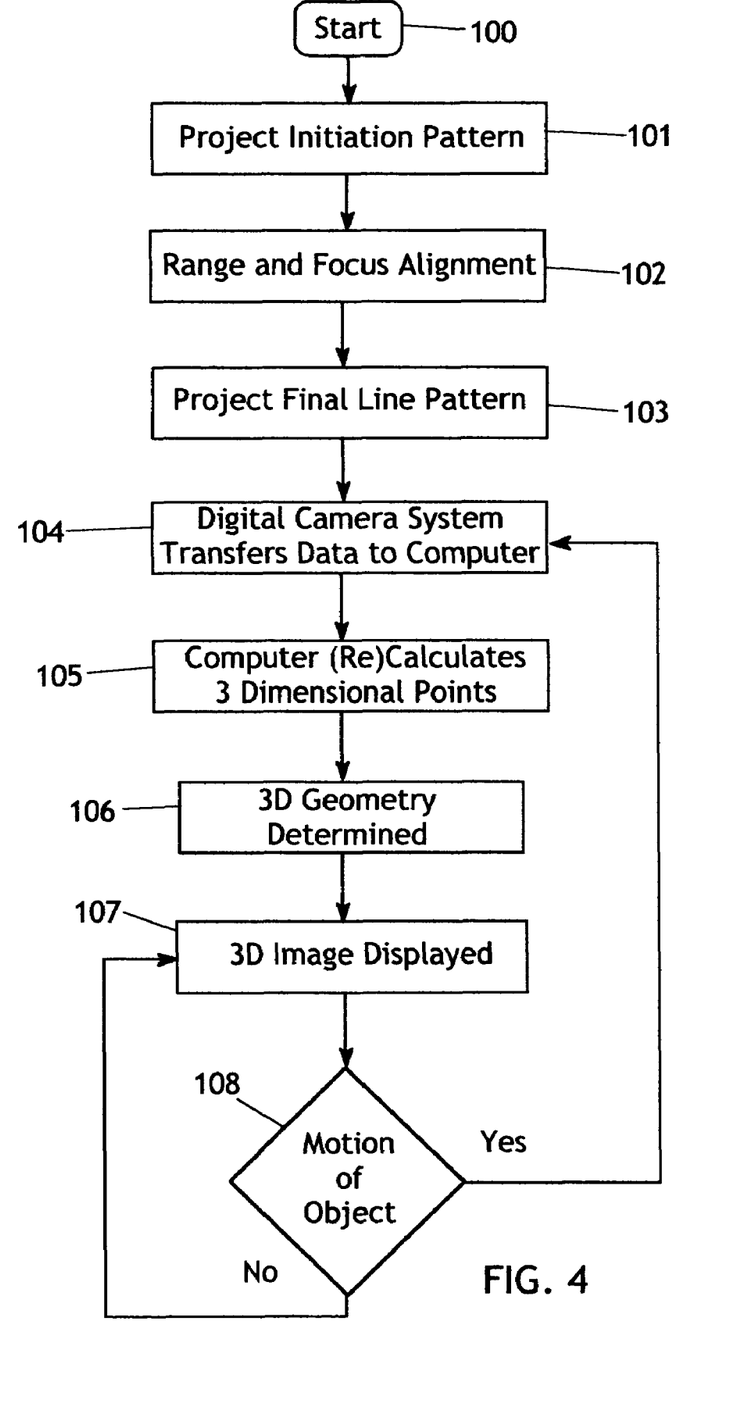
FIG. 4 is a flow chart depicting a procedure for speeding up the dynamic imaging procedure.

Referring to FIG. 4, a flow chart of the computation as controlled and calculated by the computer is shown. After the start 100, in the first step 101 the projector, controlled by the computer, projects a series of lines onto the object which is to be scanned. The digital camera system, which is synchronized through computer control, takes the initial image which is utilized to determine the range and focus alignment in step 102. After these initiation procedures which are used to calibrate the system, in step 103 the computer controlled projector projects a set of fine lines which the digital camera system images and transfers 104 to the computer. The computer then calculates in step 105 all of the distances from the camera to the surface of the object and scales these data using the scale determined by the initiation process. Using these data, the complete three dimensional geometry of the surface of the object is obtained in step 106, and a three dimensional rendering of the object is constructed and displayed in step 107 on the computer screen.

It is generally likely that the object will have some movement. Consider, a breathing human or an aircraft wing under a variable stress as simple examples. The motion causes a change in some of the pixels of the digital camera. A digital camera can, for example, take 1,000 images per second. Since the movement of the object is typically very slight in one thousandth of a second, only a few pixels in the camera will be changed in that short a time span. In step 108 the current image is subtracted from the previous image to determine which pixels have changed. There are typically only a few points that need re-calculation in the short time span. Therefore the computer can easily do the re-calculation in much less than a thousandth of a second. The new three dimensional geometry is determined 106 very rapidly, very nearly as fast as the object can move. Consequently, this system provides complete motion information about the object. In other words, three dimensional imaging is obtained in real time for moving objects.

Because a digital camera can provide data at rates of a thousandth of a second, and the computer can easily do recalculations for the incoming data at a rate of much less than a microsecond, and an object generally moves very slightly in such a short time span, three dimensional movies constructed of the machine-rendered images are practicable.

For a small change, there is no need to recalculate and re-render (107) the total image. Such changes are perturbations on the whole image as defined in mathematical analyses. Therefore these small changes in the image can be referred by the camera back to the existing pattern in the computer, and the computation 105 is limited to the changes only. That procedure greatly shortens the time needed for the display of the new image relative to recalculating all of the image data.

By this method, the variations in such objects, for example, as aircraft wings under test, testing of humans breathing patterns, and bridges under load can be analyzed in real time with all of the measurements recorded in the computer memory.

Referring to FIG. 3 again, when time permits, the system of one projector 11 and one camera 10, with or without one range finder 8 may be utilized. In this case, when it is desired to record and reconstruct the full 360° image of the object, the camera, projector and range finder may either be rotated about the object, or the object may be rotated to obtain the full 360 degree view. In some cases, one may use a single camera 10 and projector 11 and one view since one then will obtain a three dimensional image of the region of the object that is scanned.

Figure 5:
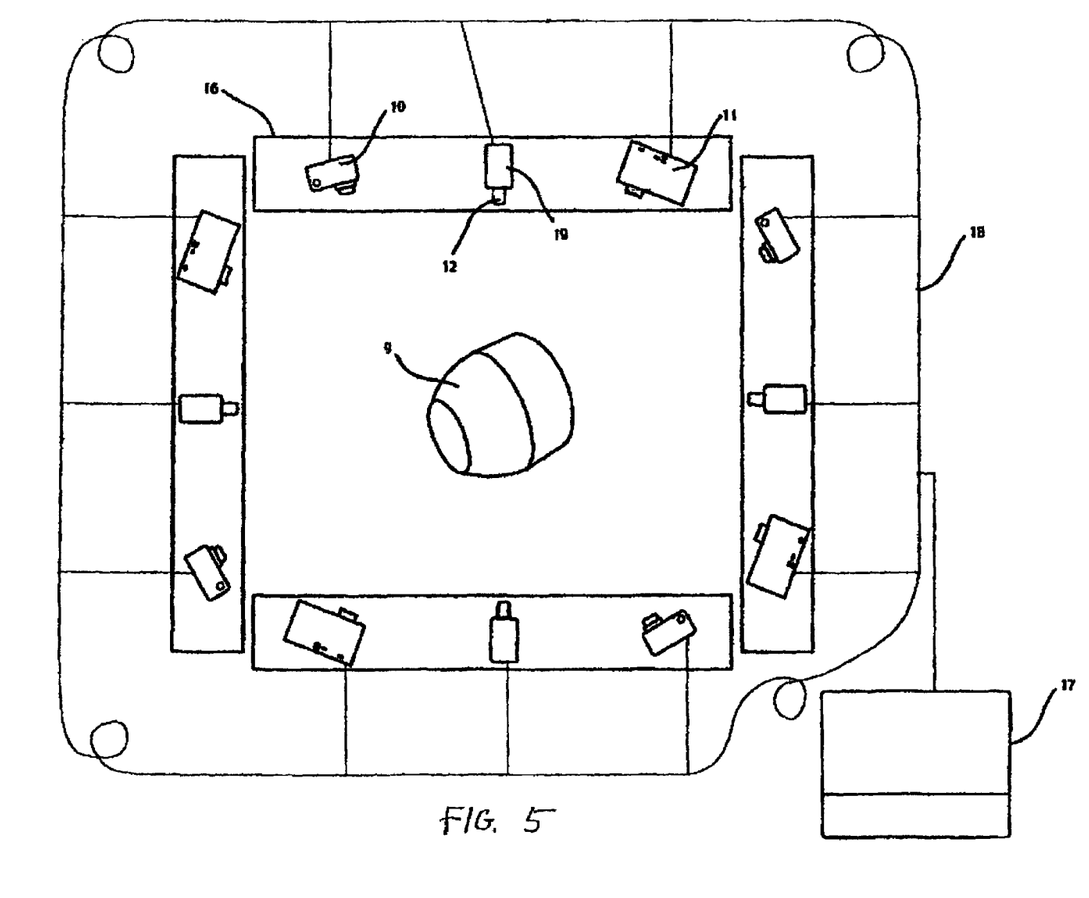
FIG. 5 is a schematic overhead view of the layout of a four projector, four camera system which can be used to obtain three dimensional dynamic images.

Referring to FIG. 5, by using four cameras 10 and four projectors 11 arrayed in generally Cartesian directions, the system can very rapidly capture the front, sides, and back views of the object 9, each of the projectors providing a computer generated pattern of lines on the object. However, in some cases, it may be adequate and economically advantageous to have three projectors and cameras. The different views are all seamlessly assembled by the computer program since each overlap of a pattern is numerically redundant and provides the same data information. Each camera can take data from any of the projected lines within its field of view.

Figures 6A, 6B:
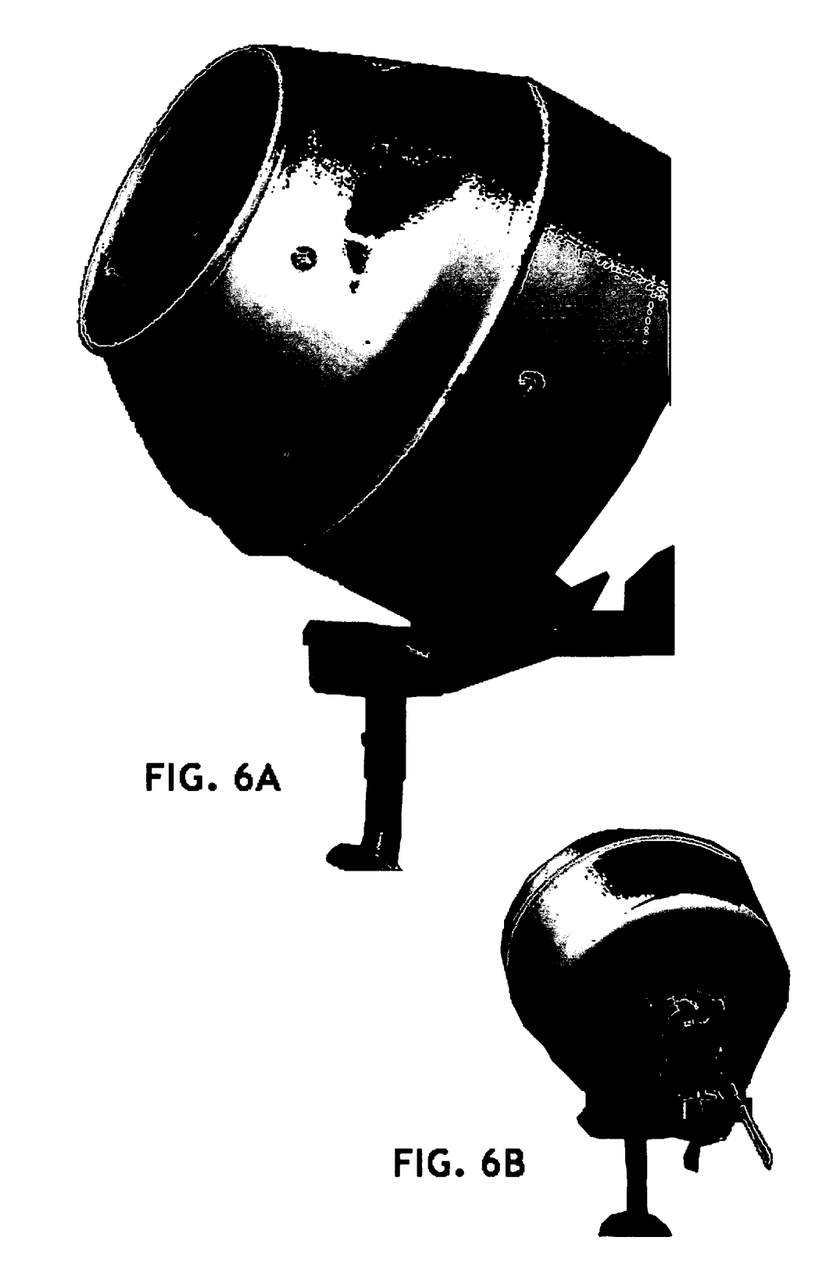
FIGS. 6A and 6B are images of a cement mixer which can be operated during the imaging procedure, using the invention to image and develop a dimensional map of the exterior surface of the mixer, and show various dynamical stresses based on dimensional variations observed in real-time.

FIG. 6A portrays the image of a cement mixer is shown in a side view. This image is reconstructed using all of the data assembled by digital camera(s) and projector(s). All of the dimensions of the cement mixer are stored, and are then utilized to rotate and re-size the cement mixer as shown in FIG. 6B.

Figure 7A:
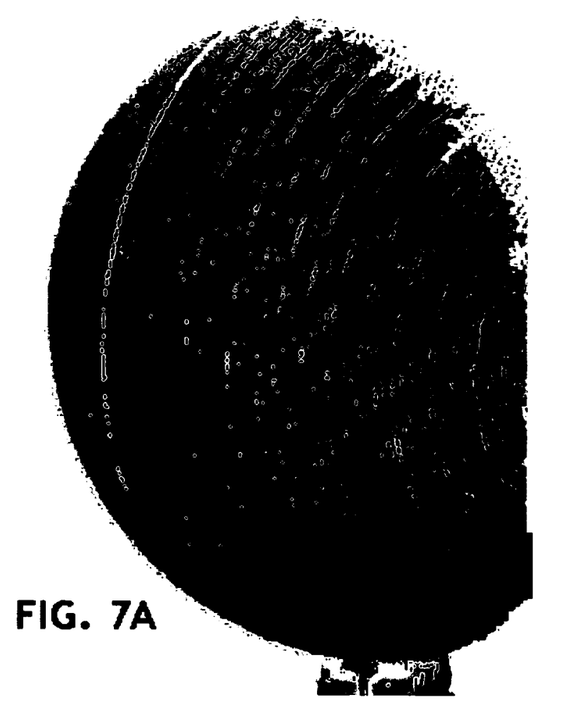
FIG. 7A is an image from a scan of a basketball.
Figure 7B:
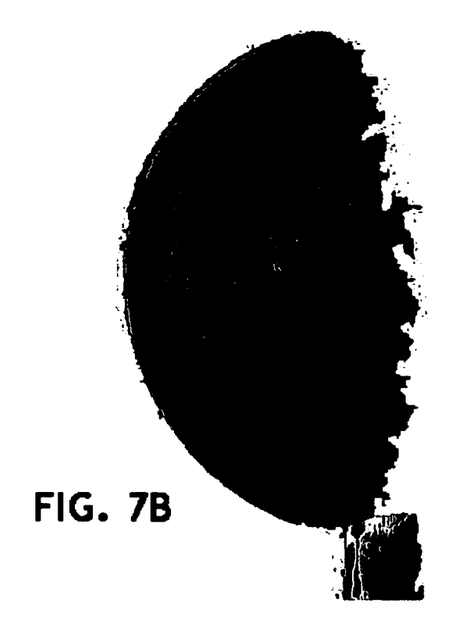
FIG. 7B is an image of the basketball computer-generated and rotated using the stored numerical dimensional data obtained from the scan procedure.

FIG. 7A depicts a three dimensional image of a portion of a basketball in a front view. All of the dimensional information of the basketball is stored in the computer, and is then utilized to rotate and compress the image as shown in FIG. 7B. Although there are no distinct surface features to note on the basketball, the fact that the rendering in any rotation is smooth and spherical is an indication of the accuracy of the method of the invention.

Figure 8A:
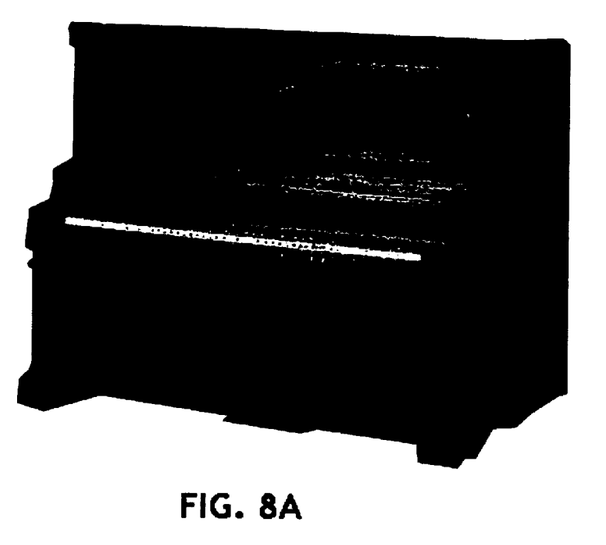
FIG. 8A is an image from a scan of an upright piano.
Figure 8B:
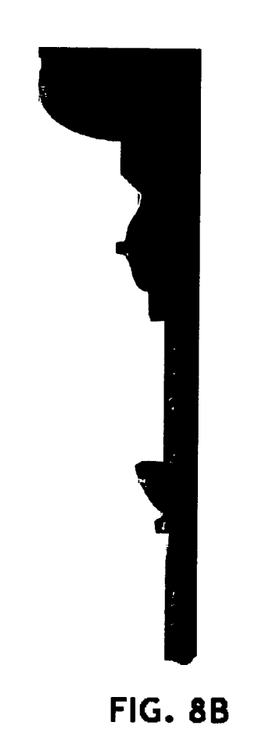
FIG. 8B is an enlarged image of the profile of the molding of the piano computer-generated from the numerical data obtained in the scan process.

FIG. 8A shows a rendered image of an upright piano based on all of the digital information about the profile of the piano determined by the method described above and stored in the computer. FIG. 8B is a magnified profile of a portion of the piano, showing in profile the relief detail of the piano molding. It is apparent that the method of the invention is capable of resolving minute surface variations over the entire object, and rendering them clearly.

Figure 9A:
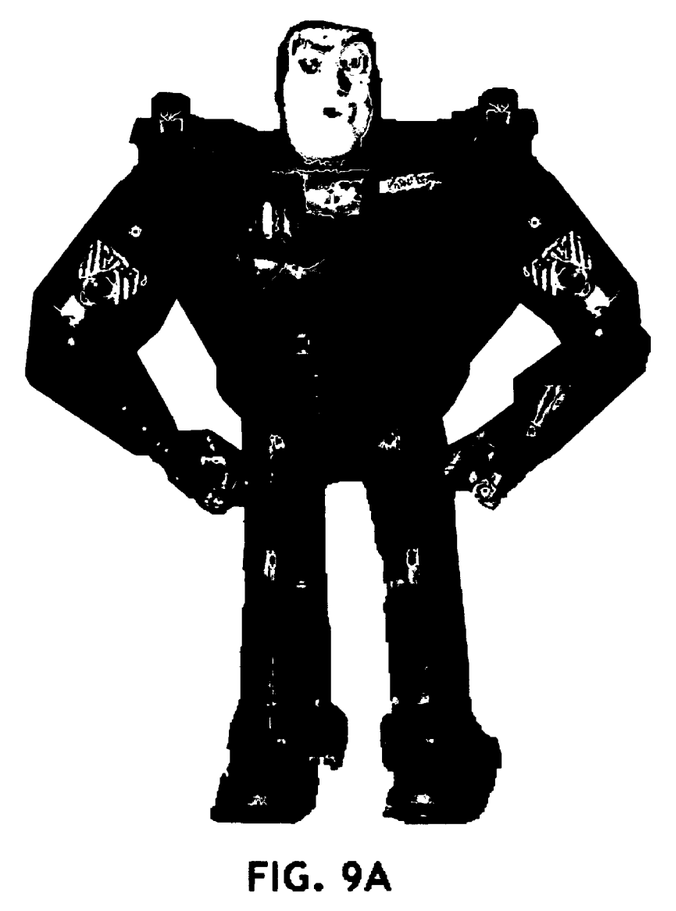
FIG. 9A is an image of an automated movie doll. The image shows the detailed set of points accumulated in the scan on the left.
Figure 9B:
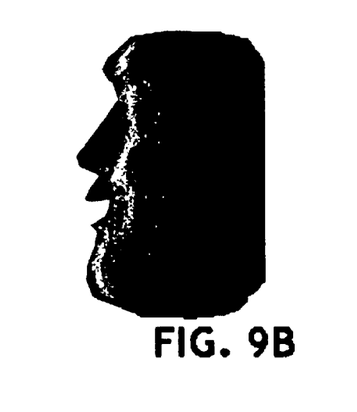
FIG. 9B is a computer rendering of the complete dimensional map image.

FIG. 9A depicts the rendered image of a toy based on all of the digital information about the profile of the toy determined by the method described above and stored in the computer. The reconstructed facial profile of the toy shown in FIG. 9B depicts the power of rendering from the dimensional database obtained by the invention.

Figure 10:
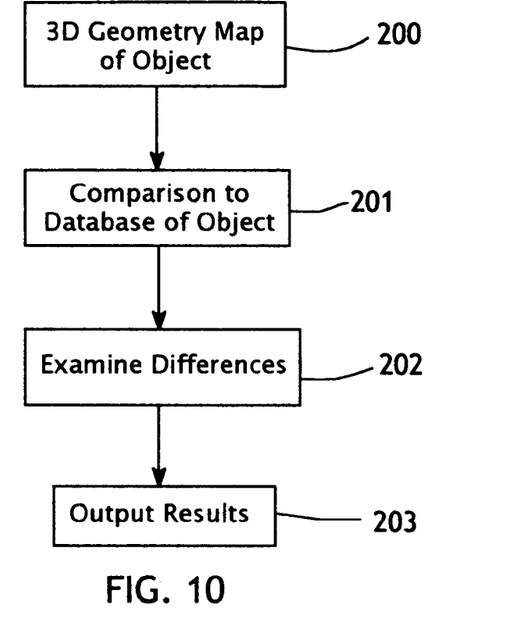
FIG. 10 is a functional block diagram depicting the general method of the present invention for generating a dimensional map of the outer surface of an object and applying the useful results therefrom.

FIG. 10 depicts a flow chart showing the general method for applying the three dimensional display and measurements of a solid object to achieve useful results. In step 200 the process of imaging and calculating the 3 D geometry of the object is carried out as described above to obtain a 3D dimensional map of the object. The map is compared to an existing database of the object in step 201. In step 202 the differences between the map and database are adjusted for a best fit and examined, and the final step 203 the differences are reported in a useful format. The object database used in step 201 may be obtained from prior records of design, CAD files, and the like, or from previous dimensional maps obtained by the invention in prior time intervals ranging from portions of a second to months. The output of step 203 may comprise a graphic map depicting changes overlaying an image of the object and portrayed in false color, or contour lines overlaying the image, or other graphic techniques that highlight areas of dimensional change and interest.

Figure 11:
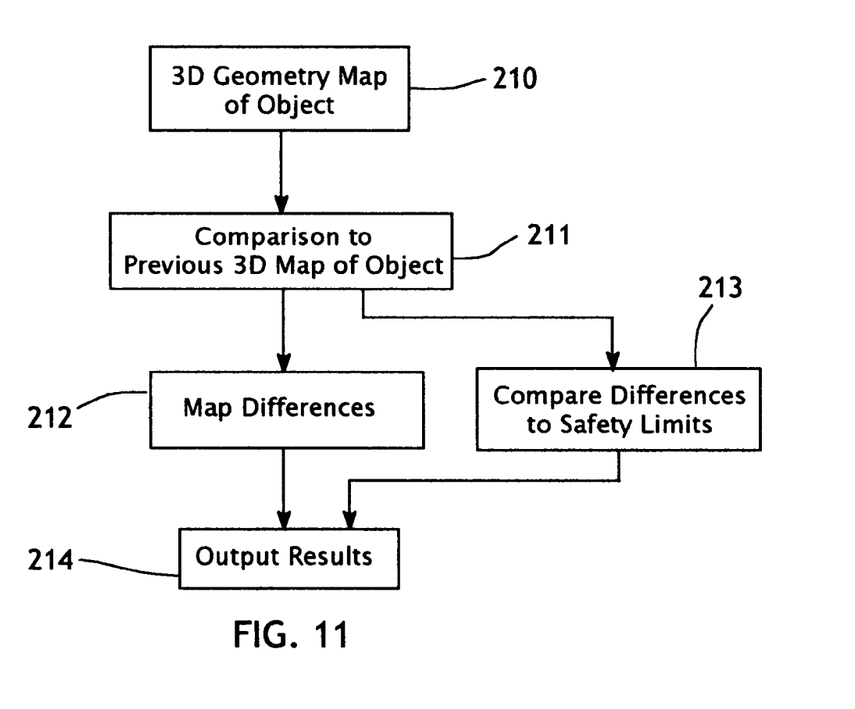
FIG. 11 is a functional block diagram depicting the method of the present invention applied to generating a dimensional map of the outer surface of a moving object.

FIG. 11 depicts a flow chart representing the dynamic imaging of an object or person in motion or exhibiting movement of at least some portion, starting at step 210 with obtaining the most recent 3D geometry map from the most recent image scan. The scan is then compared to the previous 3D map in step 211. The differences are then compared in step 212 and mapped into the output 214. In step 213 the differences are compared to a safety limit (dimensional tolerances) to determine if the object is approaching or exceeding a tolerance limit. For example, a tank undergoing pressurization may expand normally, but it may also distort in some areas, indicating a potential failure mode. In the example above of quality control processing for wallboard and sheetrock, the 3D map of the surface of each sheet may be compared to an ideal planar surface to highlight any surface defects or surface curvature. If the differences for any sheet exceed quality standards, the sheet will be rejected.

Figure 12:
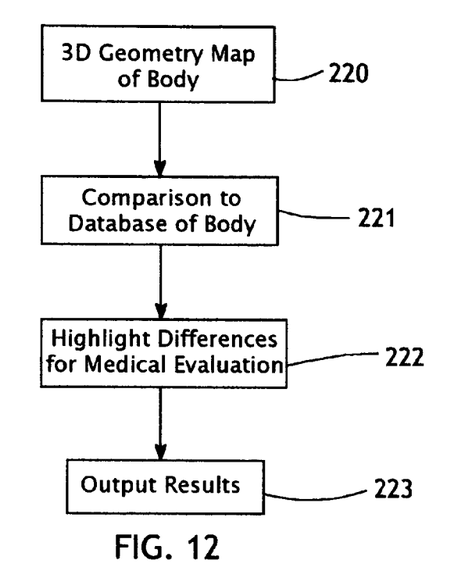
FIG. 12 is a functional block diagram depicting the method of the present invention applied to generating a dimensional map of the human body for medical purposes.

Referring to FIG. 12, a method for treating the human body begins at step 220 with imaging and calculating the 3D geometry map of the body as described above. The 3D geometry map of the body 220 is compared in step 221 to a database containing the stored 3D geometry map(s) of the body 221. The differenced are then computed and highlighted in step 222 for medical or health evaluation, and the new image is outputted 223 with the differences highlighted. This method may be used to assess changes in the body over time for medical purposes, and also may be used to evaluate weight loss programs, body building regimens, and the like.

Figure 13:
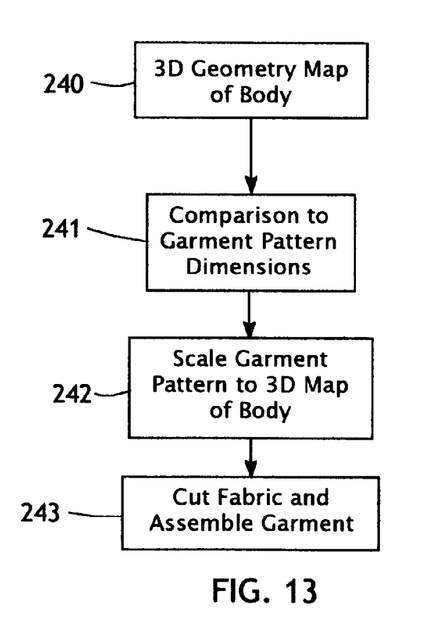
FIG. 13 is a functional block diagram depicting the method of the present invention applied to generating a dimensional map of the human body and fashioning custom clothing from the map.

Referring to FIG. 13, a method for determining sizing or custom manufacturing for a suit, dress, shoes, or other garments, begins at step 240 with imaging and calculating the 3D geometry map of the body (or relevant portion of the body). The 3D geometry map is then numerically compared in step 241 to the garment pattern dimensions. The garment pattern is then scaled in step 242 so that every seam will extend in a best fit to the mapped body. In step 243 the garment fabric is then cut according to the scaled pattern and assembled. This process produces an optimal fit to the individual body, despite the wide range in human body types and sizes. An a similar vein, the 3D geometry map of the body may be used instead to select the best fitting pre-manufactured garments, based on a complete comparison of data on existing garments with the 3D geometry body map of the invention.

Figure 14:
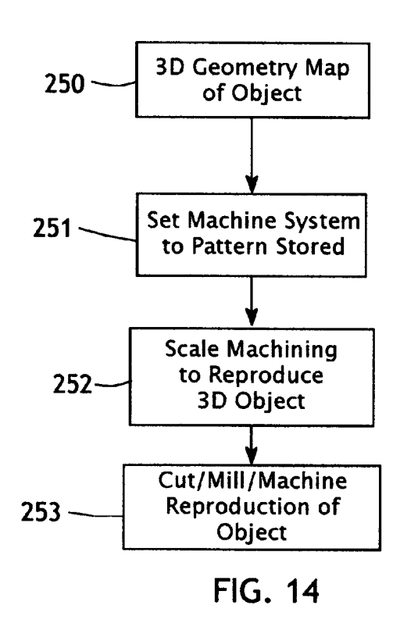
FIG. 14 is a functional block diagram depicting the method of the present invention applied to generating a dimensional map of an object and using automated machining to create from the map a copy of the object.

Referring to FIG. 14, a method for reverse engineering or reproduction of an object begins at step 250 with the initial scan provides a 3D map of the geometry of the object. The 3D geometry data is then utilized in step 251 to provide the machine data to an automated milling machine to reproduce the original object using the data of the scan. In step 252 the reproduction is then scaled to produce a reproduction equal to the original object; likewise, the reproduction may be scaled to any desired size without introducing any distortion. In step 253 the automated machine then carries out the cutting or milling to reproduce the object.

The foregoing description of the preferred embodiments of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

The invention claimed is:

1. A method for creating a three dimensional map of the surface of an object, including the step of:
   selectively projecting at least one pattern of lines on at least one portion of the surface of the object;
   digitally capturing the image of said at least one pattern on the object;
   calculating the distance of each incremental portion of the image to the object, and storing the distance data to comprise the three dimensional map;
   rendering a three dimensional image of the at least one portion of the surface of the object using the data from the three dimensional map;
   further including the step of establishing a fiducial distance from said image to said object, and scaling said distance data according to said fiducial distance;
   said step of establishing the fiducial distance including projecting a pair of parallel light rays onto said object, said pair of rays having a known spacing, said light rays forming point images on the object having the same known spacing.

2. A method for creating a three dimensional map of the surface of an object, including the step of:
   selectively projecting at least one pattern of lines on at least one portion of the surface of the object;
   digitally capturing the image of said at least one pattern on the object;
   calculating the distance of each incremental portion of the image to the object, and storing the distance data to comprise the three dimensional map;
   rendering a three dimensional image of the at least one portion of the surface of the object using the data from the thee dimensional map;
further including the step of establishing a fiducial distance from said image to said object, and scaling said distance data according to said fiducial distance;
   wherein said step of establishing the fiducial distance includes placing an object of known size adjacent to the object before projecting the at least one pattern and capturing the image.

3. The method of claim 1, wherein the step of selectively projecting includes projecting a plurality of patterns using different, respective wavelengths for each pattern, and the step of digitally capturing includes recording a plurality of images, each image being recorded in the different, respective wavelengths of said plurality of patterns.

4. The method of claim 3, wherein said steps of selectively projecting and digitally capturing occur simultaneously at all the different, respective wavelengths.

5. The method of claim 1, further including the step of comparing the three dimensional map with a data set describing the surface of the object to determine variations in the surface of the object over time.

6. The method of claim 5, where the data set comprises a previously acquired three dimensional map of the object to determine variations in the surface of the object in the time interval between the previously acquired three dimensional map and the most recent three dimensional map.

7. The method of claim 1, wherein the step of selectively projecting includes the step of providing a plurality of projectors, each projecting a pattern of lines on a respective portion of the surface of the object.

8. The method of claim 1, wherein the step of digitally capturing the image includes providing a plurality of cameras, each capturing an image of a respective portion of the surface of the object.

9. The method of claim 1, wherein the steps of digitally capturing the image, calculating the distance, and rendering a three dimensional image are performed reiteratively and sufficiently rapidly to generate a movie comprised of the three dimensional images.

10. The method of claim 9, further including providing a plurality of linked digital processors to perform the steps of calculating the distance and rendering the image.

11. The method of claim 1, further including the step of providing a computer to control the steps of selectively projecting, digitally capturing, calculating the distance, and rendering a three dimensional image.

12. The method of claim 1, further including the step of providing a computer to control the steps of selectively projecting, digitally capturing, calculating the distance, and rendering a three dimensional image, and applying the fiducial distance data to focus the at least one pattern of lines on the at least one portion of the surface of the object.

13. The method of claim 1, further including the step of reiterating the steps of digitally capturing, calculating the distance, and rendering the three dimensional object to generate a plurality of 3D renderings in sequential order.

14. The method of claim 13, further including the step of comparing each three dimensional map with a previous three dimensional map in the sequential order to determine if portions of the surface of the object have undergone movement, and if the movement does not exceed a predetermined threshold, to thereafter perform the steps of calculating the distance and rendering the three dimensional image only for those portions that have undergone movement.

15. The method of claim 13, further including the step of applying stress to the object to determine changes in the object under the stress.

16. The method of claim 1, further including the step of providing an automated machining system, and providing the three dimensional map to the automated machining system to fabricate a three-dimensional copy of the object.

17. The method of claim 1, further including the step of using a human body as the object, and applying the resulting three dimensional map to medical studies.

18. The method of claim 1, further including the step of using a human body as the object to acquire a three dimensional map of the body, comparing the three dimensional map to a database describing a garment pattern, scaling the garment pattern to provide optimal fit to the body, and cutting and assembling the scaled garment 19. The method of claim 1, further including the step of comparing the three dimensional map to a database describing the object, and determining any dimensional changes that may indicate possible structural failure of the object.

20. The method of claim 19, wherein the object is selected from a group consisting of aircraft, vehicles, ships, structures, mechanical devices, and tools.

21. The method of claim 1, further including the step of comparing the three dimensional map to a database describing the object, and determining any dimensional changes that may indicate possible security breaches.

22. The method of claim 1, wherein the surface of the object comprises the surface of an interior space.

23. The method of claim 22, wherein the object is selected from a group consisting of aircraft, motor vehicles, warehouses, ships, trains, and buildings.

\* \* \* \* \*